United States Patent [19]

Higuchi et al.

[11] Patent Number: 5,399,743
[45] Date of Patent: Mar. 21, 1995

[54] DIPEPTIDE DERIVATIVE AND PROPHYLACTIC OR THERAPEUTIC AGENT FOR BONE DISEASES CONTAINING SAME AS ACTIVE INGREDIENT

[75] Inventors: Naoki Higuchi, Yokohama; Masayuki Saitoh, Ibaraki; Shinjiro Niwata, Ibaraki; Yoshinobu Kiso, Ibaraki; Yasuhiro Hayashi, Nishi, all of Japan

[73] Assignee: Suntory Limited, Osaka, Japan

[21] Appl. No.: 121,461

[22] Filed: Sep. 16, 1993

Related U.S. Application Data

[63] Continuation of Ser. No. 69,371, Jun. 1, 1993, abandoned.

[30] Foreign Application Priority Data

Jun. 15, 1992 [JP] Japan ............... 4-155115

[51] Int. Cl.$^6$ ............... C07C 261/00; C07C 233/00
[52] U.S. Cl. ............... 560/159; 554/35; 564/192; 564/204; 564/215
[58] Field of Search ............... 560/159; 554/35; 564/192, 204; 584/215; 514/551, 563

[56] References Cited

U.S. PATENT DOCUMENTS

| | | | |
|---|---|---|---|
| 4,176,116 | 11/1979 | Hassall et al. | 560/159 |
| 4,187,216 | 2/1980 | Hassall et al. | 560/159 |
| 4,487,717 | 12/1984 | Oyama et al. | 560/159 |
| 4,778,915 | 10/1988 | Lina et al. | 560/29 |
| 4,954,634 | 9/1990 | Heinrich et al. | 548/341 |
| 5,081,284 | 1/1992 | Higuchi et al. | 560/159 |
| 5,227,401 | 7/1993 | Hanson et al. | 514/489 |

FOREIGN PATENT DOCUMENTS

| | | |
|---|---|---|
| 0130679 | 1/1985 | European Pat. Off. |
| 0504938 | 9/1992 | European Pat. Off. |
| 63-284127 | 11/1988 | Japan |
| 2-218610 | 8/1990 | Japan |
| 4-1737 | 1/1992 | Japan |
| 1206487 | 9/1970 | United Kingdom |

OTHER PUBLICATIONS

Gakushikai Kaiho, No. 792, pp. 48–52, 1991.
J. Clinical Investigation, Inc., vol. 81, Feb. 1988, 596–600 Stewart et al for "Synthetic Human Parathyroid Hormone-Like Protein etc."
Biochem J. (1980) 192, 365–368 Delaisse et al "Inhibition of bone resorption in culture by inhibitors of thiol proteinases".
Biochemical and Biophysical Research Communications vol. 125, No. 2, 1984 pp. 441–447 Delaisse et al "In Vivo and In Vitro Evidence for the Involvement etc."
Bone 8, 305–313 (1987) Delaisse et al "The Effects of Inhibitors of Cysteine-Proteinases and Collagenase etc."
Chemical Abstracts, vol. 118, No. 5, Feb. 1, 1993, Ahmed et al "Peptidyl fluoromethyl ketones . . . arthritis" p. 15, col. 1, Abstract No. 32 521s.
Chemical Abstracts, vol. 115, No. 9, Sep. 1991, Van Noorden et al "Selective inhibition of cysteine . . . octeoclasts" p. 76, col. 2, Abstract No. 85 386w.
Chemical Abstracts, vol. 110, No. 9, Feb. 1989, Angliker et al "Synthesis and properties . . . fluoromethanes" p. 709, col. 1, Abstract No. 76 058k.
Chemical Abstracts, vol. 110, No. 9, Feb. 1989, Van Noorden et al "Cysteine proteinase activity in etc" pp. 454–455, col. 2, abstract No. 73 355u.

*Primary Examiner*—Paul J. Killos
*Attorney, Agent, or Firm*—Nixon & Vanderhye

[57] ABSTRACT

A dipeptide derivative having the formula (I):

$$R^1NH-CH(R^2)-CO-NH-CH(R^3)-COCH_2F \qquad (I)$$

wherein, $R^1$ is an aliphatic acyl group having 2 to 8 carbon atoms or a benzyloxycarbonyl group; and
$R^2$ and $R^3$ are independently a hydrogen atom or a straight or branched alkyl group having 1 to 4 carbon atoms and a prophylactic or therapeutic agent containing the same as an active ingredient.

4 Claims, No Drawings

DIPEPTIDE DERIVATIVE AND PROPHYLACTIC OR THERAPEUTIC AGENT FOR BONE DISEASES CONTAINING SAME AS ACTIVE INGREDIENT

This is a continuation of Ser. No. 08/069,371, filed Jun. 1, 1993, now abandoned.

BACKGROUND OF THE INVENTION

1. Field of the Invention

The present invention relates to a dipeptide derivative and a prophylactic or therapeutic agent for bone diseases containing the same as an active ingredient.

2. Description of the Related Art

In recent years, the rapid increase in the number of aged people in the population has caused an increase in so-called geriatric diseases. Among these diseases, bone diseases including osteoporosis are accompanied by a higher incidence of bone fracture, and this has been the major cause of the increase of aged patients who are bed-ridden. Therefore, there is an urgent need for a pharmaceutical composition for preventing and treating the above-mentioned bone diseases.

Bone is not a tissue which does not undergo any change once formed. The structure and the amount of bone is maintained due to the balance between osteogenesis and bone resorption. When this balance is lost due to aging or some other factors, various bone diseases are induced. Examples of diseases due to abnormal sthenia of bone resorption include malignant hypercalcemia caused by myeloma or lymphoma, bone Paget's disease caused by local bone resorption, and osteoporosis in aged people accompanied by a decrease in bone weight, though the causes of this disease are as yet unknown.

Bones mainly comprise organic matter of collagen fibers and the inorganic matter of calcium salts. The two are combined and form bones, constructions which are highly resistant against tension and pressure. In particular, calcium salts amount to 70% of the total bone weight. In bone diseases, calcium salts tend to dissolve into the blood and thus are slowly lost as the diseases proceed. Known methods for preventing or treating these diseases comprise supplying calcium or maintaining the normal calcium level.

For the prevention or treatment of such diseases, up to now use has been made of the method of treatment of supplementing or maintaining the calcium. Use has been made of active vitamin $D_3$ preparations and calcium preparations for this. Further, hormone preparations such as estrogen and calcitonin preparations have been used in order to suppress decalcification of bones.

In addition to the above-mentioned therapeutic methods, the importance of prevention of the decrease in collagen fibers in bone diseases has been recently noted. Namely, recent studies have revealed the decomposition enzyme for collagen fiber which is contained in bones as the matrix, and attempts have been made to use an inhibitor of that decomposition enzyme for the treatment of resorption type bone diseases (see Japanese Unexamined Patent Publication (Kokai) No. 63-284127 and Japanese Unexamined Patent Publication (Kokai) No. 2-218619). It was only recently, however, that it became clear that collagen type I, which is contained in bones as the matrix, is decomposed by cathepsin L, which is a thiol protease found among lysosomal enzymes (see Nobuhiko Katsunuma, Gakushikai Kaiho, no. 792, pp. 48 to 52, 1991). These studies have just recently been concluded and no report has been made of examples of actual treatment of patients. No practical therapeutic agent has yet been provided.

SUMMARY OF THE INVENTION

The object of the present invention, in consideration of the state of the prior art mentioned above, is to provide a pharmaceutical composition which is useful for the prevention or treatment of malignant hypercalcemia, bone Paget's disease, osteoporosis, and other resorption type bone diseases. More particularly, the object of the present invention is to provide a novel compound which enables fundamental prevention and treatment by suppression of the decrease in calcium salts in the bone and to provide a prophylactic or therapeutic agent for bone diseases including the compound as an active ingredient, to take the place of the conventional method of treatment of supplementing or maintaining the calcium in resorption type bone diseases.

Another object of the present invention is to provide a prophylactic or therapeutic agent for bone diseases which enables more effective prevention and treatment of bone resorption diseases by simultaneously suppressing the decrease in calcium salts in the bone and suppressing the decrease in collagen fibers.

The present inventors previously found that an inhibitor of cathepsin L has activity to reduce the blood calcium concentration in a hypercalcemia model of rats using 1-34 fragments of parathyroid hormone-related protein (hereinafter referred to as "PTHrp(1-34)" (Journal of Clinical Investigation, 81, (2), 596-600 (1988) and Endocrinology, 123, 2841-2848 (1988)) and filed as Japanese Patent Application Nos. 3-59182 and 3-59185 (see EP-A-0504938).

The present inventors engaged in intensive research to develop a more effective compound using the above rat model and as a result discovered that a dipeptide derivative having the formula (I):

$$R^1NH\text{---}CH(R^2)\text{---}CO\text{---}NH\text{---}CH(R^3)\text{---}COCH_2F \qquad (I)$$

wherein, $R^1$ represents an aliphatic acyl group having 2 to 8 carbon atoms or a benzyloxycarbonyl group (hereinafter abbreviated as Z); and $R^2$ and $R^3$ independently represent a hydrogen atom or a straight or branched alkyl group having 1 to 4 carbon atoms has an action reducing the blood calcium concentration when administered orally or parenterally, for example, via intraperitoneal or subcutaneous administration, and thus is useful as a prophylactic or therapeutic agent of bone diseases, and thus completed the present invention.

In accordance with the present invention, there is also provided a prophylactic or therapeutic agent for bone diseases containing as an active ingredient at least one compound selected from the group of compounds of the above formula (I).

The bone diseases covered by the prophylactic or therapeutic agent of the present invention mean resorption type bone diseases. Specifically, mention may be made of malignant hypercalcemia, bone Paget's disease, and osteoporosis.

DESCRIPTION OF THE PREFERRED EMBODIMENT

In formula (I), as the aliphatic acyl group having 2 to 8 carbon atoms represented by $R^1$, mention may be made of the acetyl group, propionyl group, butyryl group, isobutyryl group, valeryl group, isovaleryl group, hexanoyl group, heptanoyl group, octanoyl group, etc. In particular, the acetyl group is preferred.

In formula (I), as the straight or branched alkyl group having 1 to 4 carbon atoms represented by $R^2$ and $R^3$, mention may be made of the methyl group, ethyl group, n-propyl group, isopropyl group, n-butyl group, isobutyl group, and sec-butyl group. In particular, it is preferable that the $R^2$ be the isobutyl group and $R_3$ be the n-butyl group.

The dipeptide derivative of the present invention may be produced as follows in accordance with Nobuo Izumiya, Tetsuo Kato, Haruhiko Aoyagi, and Michio Waki, "Fundamentals and Experiments in Peptide Synthesis", 1985 (Maruzen).

That is, an N-terminal protected dipeptide shown by formula (II):

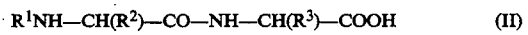

$$R^1NH\text{---}CH(R^2)\text{---}CO\text{---}NH\text{---}CH(R^3)\text{---}COOH \qquad (II)$$

wherein, $R^1$, $R^2$, and $R^3$ are as defined above is dissolved in a suitable solvent not obstructing the reaction. To this is added monofluoroacetic anhydride and a catalytic amount of 4-dialkylaminopyridine, then trialkylamine is added and a reaction caused at room temperature to 50° C., then the result is purified by column chromatography etc., whereby it is possible to obtain the corresponding dipeptide derivative expressed by the formula (I)

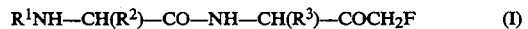

$$R^1NH\text{---}CH(R^2)\text{---}CO\text{---}NH\text{---}CH(R^3)\text{---}COCH_2F \qquad (I)$$

wherein, $R^1, R^2$, and $R^3$ are as defined above.

As an example of a suitable solvent which can be used for the reaction without inhibiting the reaction, mention may be made of benzene, toluene, tetrahydrofuran (THF), dioxane, chloroform, methylene dichloride, ethyl acetate, N,N-dimethylformamide (DMF), etc. Use of DMF is the most preferable.

As an example of the 4-dialkylaminopyridine used in the reaction, mention may be made of 4-dimethylaminopyridine, 4-pyrrolidinoaminopyridine, etc. Use of 4-dimethylaminopyridine is the most preferable.

As an example of the trialkylamine used in the reaction, mention may be made of triethylamine etc. Use of triethylamine is the most preferable.

Further, in the case of a compound having an acyl group as $R^1$, production is also possible by deprotecting Z of the corresponding dipeptide derivative, shown by the following formula (III):

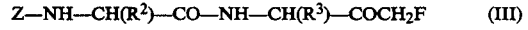

$$Z\text{---}NH\text{---}CH(R^2)\text{---}CO\text{---}NH\text{---}CH(R^3)\text{---}COCH_2F \qquad (III)$$

wherein, $R^2$ and $R^3$ are as defined above and introducing here $R^1$ using an acylhalide corresponding to the desired $R^1$, for example.

In the compound of the present invention, the carbon atoms to which $R^2$ and $R^3$ are attached, respectively, are asymmetrical carbon atoms, so there are compounds having a configuration corresponding to L- or D- amino acids, but no difference in physiological activity can be observed among compounds obtained by optical resolution of these, so use may also be used of the L-, D-, and racemic compounds, as the active ingredient of the present invention.

The active ingredient of the present invention may be administered in various forms in accordance with usual methods. As such formulations, mention may be made of orally administered preparations such as capsules, tablets, granules, fine granules, syrups, and dry syrups and parenterally administered preparations such as injections, rectal suppositories, vaginal suppositories, and other suppositories, sprays and other nasal preparations, and ointments, transdermal absorption tapes, and other transdermal absorption preparations.

The carrier usable in the preparation of the present prophylactic or therapeutic for bone diseases may be any conventional carriers. Examples of such carriers are starch, lactose, sucrose, sorbitol, talc, stearic acid, magnesium stearate, microcrystalline cellulose, sodium laurate, sodium tartarate, synthetic or natural gums such as tragacanth, acacia, alginate, dextran, methylcellulose, sodium carboxymethylcellulose, polyvinylpyrrolidone and gelatin, dicalcium phosphate, water, injectable water, buffered physiological saline, ethanol, glycerine, syrup, edible oils such as cottonseed oil, sesame oil, coconut oil and peanut oil, natural or semisynthetic fat such as cacao butter, Witepsol and Macrogol, mineral oil, paraffin, vaseline, wax and so on. Although these are not limitations to the content of the active component in the composition, the preferable content is 0.5 to 90% by weight based upon the total weight of the composition.

In the administration of the preparation of the present invention, as the above-mentioned active ingredient, it is sufficient to administer orally or parenterally 1 to 1000 mg/kg, preferably 1 to 100 mg/kg, more preferably 5 to 50 mg/kg, per day for a normal adult, divided into three portions. The amount of administration can be suitably adjusted according to the age of the patient, the state of the disease, etc.

The compound of the present invention is a low molecular weight dipeptide derivative, so the toxicity is low. For example, the acute toxicity $LD_{50}$ of the compound 1 shown in Table 1 in 20 hours after oral administration to rats is over 1 g/kg.

The active ingredient of the present invention normalizes the blood calcium concentration in rat hypercalcemia induced by PTHrp(1-34). PTHrp (parathyroid hormone-related protein) is a protein identified as the factor inducing hypercalcemia in humans. The fragment comprised of the 1 to 34th amino acid residues, that is, PTHrp(1-34), is the active type. The PTHrp(1-34) promotes bone resorption in vitro and induces hypercalcemia if administered to rats. Further, since a bone resorption promoting action is exhibited in vitro (see Journal of Clinical Investigation, 81, (2), 596-600 (1988) and Endocrinology, 123, 2841-2848 (1988)), it is possible to use this for a model of osteoporosis.

Using this model, the compound of the present invention was administered to Wistar rats, then PTHrp(1-34) was administered and the blood calcium concentration was measured after one hour after administration. From this, it was learned that the group to which the compound of the present invention had been administered has a significantly lowered blood calcium concentration compared with the group treated with only PTHrp(1-34). That is, the compound of the present invention suppresses hypercalcemia induced by PTHrp(1-34), so is useful as a prophylactic or therapeutic agent for bone diseases.

Further, Japanese Examined Patent Publication No. 4-1737 discloses as an inhibitor of cysteine protease including cathepsin L, the compound where in formula (I) $R^1$ is Z, $R^2$ is the benzyl group, and $R^3$ is the methyl group, that is, 3-(N-benzyloxycarbonyl-phenylalanylamide)-1-fluoro-2-butanone (hereinafter abbreviated as Z-Phe-Ala-CH$_2$F). This compound, as clear from the following examples, however, did not exhibit any action of normalizing the calcium concentration in this model. This shows that the cathepsin L inhibitor is not always useful as a prophylactic or therapeutic agent for all bone diseases.

EXAMPLES

Below, the present invention will be explained in further detail based on the Examples, but of course the present invention is not limited to these Examples.

Example 1

Production of
3-(N-benzyloxycarbonyl-leucylamide)-1-fluoro-2-heptanone (hereinafter referred to as Z-Leu-Nle-CH$_2$F)

N-benzyloxycarbonyl-leucylnorleucine (3.4 g), obtained by a known method described in, for example, the above-mentioned "Fundamentals and Experiments in Peptide Synthesis", monofluoroacetic anhydride (3.8 g) and 4-dimethylaminopyridine (0.1 g) were dissolved in DMF (2 ml). To this was added triethylamine (3 ml) and the mixture was agitated for 30 minutes at 50° C. After the end of the reaction, the solvent was distilled off, then ethyl acetate (200 ml) was added to the residue to dissolve the same. This was washed with a 10% aqueous citric acid solution, a 5% sodium hydrogencarbonate, then a saturated saline water in this order, then was dried on anhydrous sodium sulfate and the solvent distilled off under a reduced pressure. The residue was purified by silica gel medium pressure column chromatography to obtain the above-referenced compound Z-Leu-Nle-CH$_2$F (compound 1: 2.3 g, 5.8 mmole) at a yield of 58%.

Example 2

Production of
3-(N-acetyl-leucylamide)-1-fluoro-2-heptanone (hereinafter referred to as Ac-Leu-Nle-CH$_2$F)

N-acetyl-leucylnorleucine (3.1 g), obtained by a known method, monofluoroacetic anhydride (3.8 g), and 4-dimethylaminopyridine (0.1 g) were dissolved in DMF (2 ml). To this was added triethylamine (3 ml) and the mixture was agitated for 30 minutes at 50° C. After the end of the reaction, the solvent was distilled off, then ethyl acetate (200 ml) was added to the residue to dissolve the same. This was washed by a 10% aqueous citric acid solution, a 5% sodium hydrogencarbonate, then a saturated saline water in this order, then was dried on anhydrous sodium sulfate and the solvent distilled off under a reduced pressure. The residue was purified by silica gel medium pressure column chromatography to obtain the above-referenced compound Ac-Leu-Nle-CH$_2$F (2.0 g, 6.6 mmole) at a yield of 60%.

Example 3

Production of
3-(N-benzyloxycarbonyl-leucylamide)-1-fluoro-5-methyl-2-hexanone (hereinafter referred to as Z-Leu-Leu-CH$_2$F)

N-benzyloxycarbonyl-leucylnorleucine (1.5 g), obtained by a known method, monofluoroacetic anhydride (1.1 g), and 4-dimethylaminopyridine (0.1 g) were dissolved in DMF (5 ml). To this was added triethylamine (1.1 ml) and the mixture was agitated for 30 minutes at 50° C. After the end of the reaction, the solvent was distilled off, then ethyl acetate (200 ml) was added to the residue to dissolve the same. This was washed by a 10% aqueous citric acid solution, a 5% sodium hydrogencarbonate, then saturated saline water in this order, then was dried on anhydrous sodium sulfate and the solvent distilled off under a reduced pressure. The residue was purified by silica gel medium pressure column chromatography to obtain the above-referenced compound Z-Leu-Leu-CH$_2$F (0.78 g, 2.0 mmole) at a yield of 50%.

Example 4

Production of
3-(N-acetyl-leucylamide)-1-fluoro-5-methyl-2-hexanone (hereinafter referred to as Ac-Leu-Leu-CH$_2$F)

N-acetyl-leucylnorleucine (1.4 g), obtained by a known method, monofluoroacetic anhydride (1.4 g), and 4-dimethylaminopyridine (0.1 g) were dissolved in DMF (10 ml). To this was added triethylamine (1.4 ml) and the mixture was agitated for 30 minutes at 50° C. After the end of the reaction, the solvent was distilled off, then ethyl acetate (200 ml) was added to the residue to dissolve the same. This was washed by a 10% aqueous citric acid solution, a 5% sodium hydrogencarbonate, then a saturated saline water in this order, then was dried on anhydrous sodium sulfate and the solvent distilled off under a reduced pressure. The residue was purified by silica gel medium pressure column chromatography to obtain the above-referenced compound Ac-Leu-Leu-CH$_2$F (0.32 g, 1.1 mmole) at a yield of 22%.

Example 5

Production of
3-(N-octanoyl-leucylamide)-1-fluoro-5-methyl-2-hexanone (hereinafter referred to as Octanoyl-Leu-Leu-CH$_2$F)

The Z-Leu-Leu-CH$_2$F (0.39 g) obtained in Example 3 was dissolved in acetic acid (5 ml) including a 25% anhydrous hydrogen bromide and the mixture was agitated at room temperature for 3 hours. After the end of the reaction, the solvent was distilled off and the resultant residue was dissolved in anhydrous methylene chloride (5 ml). To this, under ice water, were added triethylamine (0.23 g) and octanoylchloride (0.2 g) to dissolve it, then this was washed with a 10% aqueous citric acid solution, a 5% sodium hydrogencarbonate, then a saturated saline water in this order, then was dried on anhydrous sodium sulfate and the solvent distilled off under reduced pressure. The residue was purified by silica gel medium pressure column chromatography to obtain the above-referenced compound Octanoyl-Leu-Leu-CH$_2$F (200 mg, 0.52 mmole) at a yield of 52%.

Example 6

Production of
3-(N-octanoyl-leucylamide)-1-fluoro-2-heptanone (hereinafter referred to as Octanoyl-Leu-Nle-CH$_2$F)

The Z-Leu-Nle-CH$_2$F (0.29 g) obtained in Example 1 was dissolved in acetic acid (4.5 ml) including 25% anhydrous hydrogen bromide and the mixture was agitated at room temperature for 3 hours. After the end of the reaction, the solvent was distilled off and the resultant residue was dissolved in anhydrous methylene chloride (5 ml). To this, under ice water cooling, were added triethylamine (0.20 g) and octanoylchloride (0.12 g) to dissolve it, then this was washed with a 10% aqueous citric acid solution, a 5% sodium hydrogencarbonate, then a saturated saline water in this order, then was dried on anhydrous sodium sulfate and the solvent distilled off under a reduced pressure. The residue was purified by silica gel medium pressure column chromatography to obtain the above-referenced compound Octanoyl-Leu-Nle-CH$_2$F (120 mg, 0.31 mmole) at a yield of 42%.

The physical properties of these compounds are shown in Table 1.

TABLE 1

| Example No. | Chemical Structure | Properties (melting point °C.) | $^1$H-NMR (δ-ppm, TMS Standard) |
|---|---|---|---|
| Ex. 1 | [benzyloxycarbonyl-Leu-Nle-CH$_2$F structure] | Colorless Crystal (124–126) | 0.75–1.80(18H, m), 4.25(1H, m), 4.71(1H, m), 4.98(2H, d, J=48Hz), 5.16(1H, m), 5.17(2H, s), 6.54(1H, m), 7.39(5H, s). (Solvent: dichloroform) |
| Ex. 2 | [acetyl-Leu-Nle-CH$_2$F structure] | Colorless crystal (125–127) | 5.02–1.90(18H, m), 2.02(3H, s), 4.30–4.90(2H, m), 4.96(2H, d, J=47Hz), 5.75(1H, m), 6.25(1H, m). (Solvent: dichloroform) |
| Ex. 3 | [benzyloxycarbonyl-Leu-Leu-CH$_2$F structure] | Oily substance | 0.90–1.70(18H, m), 4.22(1H, m), 4.85(1H, m), 4.96(2H, d, J=47Hz), 5.12(2H, s), 5.20(1H, m), 6.56(1H, m), 7.35(5H, s) (Solvent: dichloroform) |
| Ex. 4 | [acetyl-Leu-Leu-CH$_2$F structure] | Oily substance | 0.95–1.85(18H, m), 2.02(3H, s), 4.52(1H, m), 4.80(1H, m), 4.99(2H, d, J=47Hz), 6.10 (1H, m), 6.86(1H, m). (Solvent: dichloroform) |
| Ex. 5 | CH$_3$(CH$_2$)$_6$-CO-NH-Leu-Leu-CH$_2$F structure | Oily substance | 0.82–1.90(31H, m), 2.10–2.38(2H, m), 4.46–4.96(2H, m), 5.02(2H, d, J=48Hz), 6.00(1H, m), 6.80, 7.00(total 1H, bothd). (Solvent: dichloroform) |

TABLE 1-continued

| Example No. | Chemical Structure | Properties (melting point °C.) | $^1$H-NMR (δ-ppm, TMS Standard) |
|---|---|---|---|
| Ex. 6 | CH$_3$(CH$_2$)$_6$-C(O)-NH-CH(CH$_2$CH(CH$_3$)$_2$)-C(O)-NH-CH((CH$_2$)$_3$CH$_3$)-C(O)-CH$_2$F | Oily substance | 0.88–0.97(12H, m), 1.28–1.90(19H, m), 2.17–2.25(2H, m), 4.43–4.54(1H, m), 4.72–4.82 (1H, m), 4.95(2H, d, J=48Hz), 5.30(1H, m), 6.31(1H, m). (Solvent: dichloroform) |

Example 7

Effect of Prophylactic and Therapeutic Agent of Present Invention on Rat Hypercalcemia Induced by PTHrp(1–34) (Oral Administration)

To Wistar rats (5 weeks old, male, 90 to 110 g, 5 animals in each group), 40 mg/kg body weight of the compounds listed in Table 1 were administered orally. Four hours later, 5 nmole/kg of PTHrp(1–34) was intravenously injected. One hour after the administration of PTHrp(1–34), a blood sample was collected from each animal and the blood calcium concentration was measured by the octocresolphthalein complexone method.

Note that for reference, a similar evaluation was made of L-trans-epoxysuccinyl-L-leucineamide (e-guanide)-butane (E-64) Japanese Unexamined Patent Publication (Kokai) No. 63-284127 and the Z-Phe-Ala-CH$_2$F described in Japanese Examined Patent Publication (Kokoku) No. 4-1737.

The results are shown in Table 2. The compound of the present invention and E-64 significantly suppressed the rise in the blood calcium concentration, but Z-Phe-Ala-CH$_2$F did not exhibit an activity in the evaluation system.

TABLE 2

Effect on Hypercalcemia (Oral Administration)

| Group | Compound | PTH-rp processing | Ca conc. ± standard error (mg/dl)[1] |
|---|---|---|---|
| 1 | None | Yes | 11.87 ± 0.14 |
| 2 | None | No | 11.42 ± 0.14 |
| 3 | Z-Leu-Nle-CH$_2$F[2] | Yes | 11.09 ± 0.14** |
| 4 | Ac-Leu-Nle-CH$_2$F[2] | Yes | 10.49 ± 0.09** |
| 5 | Z-Phe-ALa-CH$_2$F[3] | Yes | 12.02 ± 0.20 |
| 6 | E-64[4] | Yes | 11.09 ± 0.14** |

[1] Average blood calcium concentration ± standard error (n = 5)
[2] Compound of present invention
[3] Compound described in Japanese Examined Patent Publication (Kokoku) No. 4-1737
[4] Compound described in Japanese Unexamined Patent Publication (Kokai) No. 63-284127
**: P < 0.01 vs blood calcium concentration of first group

Example 8

Effect of Prophylatic or Therapeutic Agent of Present Invention on Rat Hypercalcemia Induced by PTHrp(1–34) (Subcutaneous Administration)

In the same way as Example 7, to Wistar rats (5 weeks old, male, 90 to 110 g, 5 animals in each group), 40 mg/kg body weight of the compounds listed in Table 1 were administered subcutaneously at the back. Two hours later, 5 nmole/kg of PTHrp(1–34) was intravenously injected. One hour after the administration of PTHrp(1–34), a blood sample was collected from each animal and the blood calcium concentration was measured by the octocresolphthalein complexone method.

TABLE 3

Effect on Hypercalcemia (Subcutaneous Administration)

| Group | Compound | PTH-rp processing | Ca conc. ± standard error (mg/dl)[1] |
|---|---|---|---|
| 1 | None | Yes | 11.28 ± 0.08 |
| 2 | None | No | 10.68 ± 0.09 |
| 3 | Ac-Leu-Nle-CH$_2$F[2] | Yes | 10.13 ± 0.11** |
| 4 | E-64[3] | Yes | 10.20 ± 0.09** |

[1] Average blood calcium concentration ± standard error (n = 5)
[2] Compound of present invention
[3] Compound described in Japanese Unexamined Patent Publication (Kokai) No. 63-284127
**: P < 0.01 vs blood calcium concentration of first group As shown in Table 2 and Table 3, the compound of the present invention significantly suppressed the blood calcium concentration both when administered orally and administered subcutaneously. This finding strongly suggests that the compound of the present invention can prevent or suppress malignant humoral hypercalcemia. The compound of the present invention is clearly useful as a prophylactic or therapeutic agent for bone diseases.

Example 9

Production of Tablets

| [Formulation] | |
|---|---|
| Compound of Example 2 | 100.0 g |
| Microcrystalline cellulose | 22.5 g |
| Magnesium stearate | 2.5 g |
| Total | 125.0 g |

The above ingredients were mixed together and punched into tablets by a tablet machine to obtain tablets of a diameter of 9 mm and weight of 250 mg containing 200 mg of the compound of Example 2.

Example 10

Production of Granules

| [Formulation] | |
|---|---|
| Compound of Example 2 | 30 g |
| Lactose | 265 g |
| Magnesium stearate | 5 g |
| Total | 300 g |

The above ingredients were mixed together well, the mixture was compression molded, then was pulverized, granulated, and sieved to obtain an excellent 10 percent granular preparation of 20 to 50 mesh.

Example 11

Production of Capsules

| [Formulation] | |
|---|---|
| Compound of Example 2 | 100 parts (by weight) |
| Potato starch | 148 parts |
| Magnesium stearate | 2 parts |

The above ingredients were thoroughly mixed in an agitator and then filled into #1 hard gelatin capsules in amounts of 250 mg each to obtain capsules containing 0 mg of the compound of Example 2.

Example 12

Production of Rectal Suppository

Witepsol H-15 (made by Dynamite Nobel Co.) was melted by heat. To this, the compound of Example 2 was added to give a concentration of 12.5 mg/ml. This was homogeneously mixed, then 2 ml portions were poured into a rectal suppository mold and cooled. This gave rectal suppositories containing the compound of Example 2 in an amount of 25 mg per preparation.

As clear from the above explanation, it was confirmed that the dipeptide derivative of the formula (I) according to the present invention can prevent or suppress malignant humoral hypercalcemia and is useful as a prophylactic or therapeutic agent for bone diseases.

We claim:

1. A dipeptide derivative having the formula (I):

$$R^1NH-CH(R^2)-CO-NH-CH(R^3)-COCH_2F \quad (I)$$

wherein, $R^1$ represents an aliphatic acyl group having 2 to 8 carbon atoms or a benzyloxycarbonyl group; and $R^2$ and $R^3$ independently represent a hydrogen atom or a straight or branched alkyl group having 1 to 4 carbon atoms.

2. A dipeptide derivative as claimed in claim 1, wherein $R^2$ is an isobutyl group and $R^3$ is an n-butyl group.

3. A prophylactic or therapeutic composition for bone diseases comprising a prophylactically or therapeutically effective amount of compound according to claim 1, as an active ingredient, and a carrier therefor.

4. A prophylactic or therapeutic composition as claimed in claim 3, wherein the bone disease is malignant hypercalcemia, bone Paget's disease, or osteoporosis.

* * * * *